US010883123B2

(12) United States Patent
Tracy et al.

(10) Patent No.: US 10,883,123 B2
(45) Date of Patent: *Jan. 5, 2021

(54) INTEGRATED WET-MILL METHOD FOR THE PRODUCTION OF ETHANOL AND SINGLE CELL PROTEIN

(71) Applicant: White Dog Labs, Inc., New Castle, DE (US)

(72) Inventors: Bryan P. Tracy, Wilmington, DE (US); Shawn William Jones, Bear, DE (US); John Randall Phillips, Middletown, DE (US); Daniel Knox Mitchell, Wilmington, DE (US); Aharon M. Eyal, Jerusalem (IL)

(73) Assignee: White Dog Labs, Inc., New Castle, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/002,674

(22) Filed: Jun. 7, 2018

(65) Prior Publication Data

US 2018/0355384 A1 Dec. 13, 2018

Related U.S. Application Data

(60) Provisional application No. 62/517,479, filed on Jun. 9, 2017.

(51) Int. Cl.
| | | |
|---|---|---|
| C12P 21/00 | (2006.01) | |
| C12P 13/08 | (2006.01) | |
| C12P 7/10 | (2006.01) | |
| C12P 7/56 | (2006.01) | |
| C12P 7/14 | (2006.01) | |
| C12R 1/145 | (2006.01) | |
| C12P 7/54 | (2006.01) | |
| C12N 1/20 | (2006.01) | |
| C12N 1/00 | (2006.01) | |
| C12P 39/00 | (2006.01) | |
| C12P 7/06 | (2006.01) | |
| C12P 19/02 | (2006.01) | |
| C12P 19/14 | (2006.01) | |

(52) U.S. Cl.
CPC .............. *C12P 7/14* (2013.01); *C12N 1/00* (2013.01); *C12N 1/20* (2013.01); *C12P 7/06* (2013.01); *C12P 7/10* (2013.01); *C12P 7/54* (2013.01); *C12P 7/56* (2013.01); *C12P 13/08* (2013.01); *C12P 19/02* (2013.01); *C12P 19/14* (2013.01); *C12P 21/00* (2013.01); *C12P 39/00* (2013.01); *C12R 1/145* (2013.01)

(58) Field of Classification Search
None
See application file for complete search history.

(56) References Cited

U.S. PATENT DOCUMENTS

| 4,439,525 A | 3/1984 | Shay et al. |
|---|---|---|
| 5,985,336 A | 11/1999 | Ivey et al. |
| 2005/0163802 A1 | 7/2005 | Jorgensen et al. |
| 2007/0141083 A1 | 6/2007 | Berge et al. |
| 2009/0291469 A1 | 11/2009 | David |
| 2014/0206058 A1* | 7/2014 | Tewalt ............... C12P 1/02 435/171 |

FOREIGN PATENT DOCUMENTS

WO 2018/204792 A2 11/2011

OTHER PUBLICATIONS

"The Corn Refining Process" Corn Refiners Association available from https://corn.org/wp-content/uploads/2009/11/CornRefiningProcess.pdf (Year: 2009).*
C Wittmann et al. "The L-Lysine Story: From Metabolic Pathways to Industrial Production", Microbiol. Monogr. pp. 1-32 (Year: 2007).*
Anupama et al. (2000). Value-added food: single cell protein. Biotechnol. Adv. 18, 459-479 (Year: 2000).*
M.G. Tyler et al. "Clostridum pasteurianum as a Source of Single Cell Protein", Canadian Federation of Biological Societies Proceedings, 19:162 (Year: 1976).*
"Acetogen." Merriam-Webster.com Dictionary, Merriam-Webster, https://www.merriam-webster.com/dictionary/acetogen. Accessed Apr. 30, 2020 (Year: 2020).*
Wikipedia entry for Clostridium pasteurianum. Retrieved from "https://en.wikipedia.org/w/index.php?title=Clostridium_pasteurianum &oldid=950800827" on Apr. 30, 2020 (Year: 2020).*
Gao, "Improved nutritional value of fish feed with plant protein ingredients by means of organic acid salts and solid state fermentation", 2011, Depart. of Animal and Aquacultural Sciences Norwegian University of Life Sciences, pp. 1-24.
International Search Report and Written Opinion issued with respect to PCT/US2018/031101, dated Oct. 19, 2018.
U.S. Appl. No. 62/502,073, filed May 5, 2017.
U.S. Appl. No. 62/517,479, filed Jun. 9, 2017.

* cited by examiner

*Primary Examiner* — Rebecca E Prouty
(74) *Attorney, Agent, or Firm* — Eva Leah Taksel (57) ABSTRACT

An integrated wet-mill method for the production of ethanol and single cell protein. An integrated method for the production of ethanol and a single cell protein product is described including providing corn kernels, which kernels comprise germ, fiber, protein and starch and which method includes, among other things, steeping said corn kernels and separating said steeped kernels from a steep liquor.

16 Claims, 2 Drawing Sheets

Fig. 1

Fig. 2

INTEGRATED WET-MILL METHOD FOR THE PRODUCTION OF ETHANOL AND SINGLE CELL PROTEIN

The instant application claims the benefit of priority under 35 U.S.C. § 119(e) of U.S. provisional application No. 62/517,479, filed Jun. 9, 2017, the disclosure of which is hereby expressly incorporated by reference hereto in its entirety.

BACKGROUND OF THE INVENTION

Protein is an essential part of any diet. Increasing world population increases the demand for protein. Vegetable proteins are less attractive sources, since they are relatively poor in some essential amino acids, e.g. lysine, methionine, tryptophan and tyrosine. Animal sources provide the full range of essential amino acids needed by humans in sufficient quantities. The way in which protein is produced has significant impacts on both the environment and human health. Fish and seafood are a critical source of protein for 3 billion people, but the ocean's supply has reached its limit. Farmed fish is likely to make up the gap and is predicted to represent ⅔ of global supply by 2030. Fish is an efficient converter of feed to gained mass (a ratio of 1.2 compared to 6 for cows), but fish farming is fast reaching its limit as well. Farmed fish is heavily dependent on wild caught fish for feed (fishmeal), which provides protein and fish oil.

Additionally, increased population increases the need for ethanol as a green fuel. An integrated and synergistic production of ethanol with high value proteins sources is highly desired. Single-cell protein is such source of high-value proteins.

SUMMARY OF THE INVENTION

Provided is an integrated method for the production of ethanol and a single cell protein product, comprising (i) providing corn kernels, which kernels comprise germ, fiber, protein and starch; (ii) steeping said corn kernels, whereby steeped corn kernels and steep liquor are formed; (iii) separating said steeped kernels from said steep liquor, whereby separated steeped kernels and separated steep liquor are formed, which separated steep liquor comprises a first carbon source; (iv) optionally, concentrating said separated steep liquor by water removal therefrom, whereby concentrated steep liquor is formed; (v) mechanically separating germ from said separated steeped kernel, whereby separated germ is formed; (vi) mechanically separating fiber from said separated steeped kernel, whereby separated fiber is formed, which separated fiber comprises a second carbon source; (vii) optionally, blending separated fiber with separated steep liquor and/or with concentrated steep liquor, whereby a first blend is formed; (viii) separating starch from protein in said steeped kernel, whereby separated starch and a separated protein composition are formed, which separated protein composition comprises a third carbon source and which separated starch comprises a fourth carbon source; (ix) cooking and liquefying said separated starch, whereby liquefied starch is formed; (x) saccharifying said liquefied starch to a glucose solution; (xi) culturing yeast in said glucose solution for a specific duration, whereby CO2 and an ethanol comprising fermentation liquor are formed; (xii) distilling ethanol from said fermentation liquor, whereby separated ethanol and stillage are formed, which stillage comprising a fifth carbon source, which fifth carbon source comprises residual carbohydrate and optionally byproduct glycerol, (xiii) optionally, blending separated fiber with separated steep liquor and/or with concentrated steep liquor and with said stillage, whereby a second blend is formed; (xiv) providing a fermentation medium comprising at least one carbon source selected from the group consisting of (a) said first carbon source; (b) said second carbon source; (c) said third carbon source; (d) said fourth carbon source; (e) liquefied starch; (f) glucose solution, and (g) said fifth carbon source; and optionally CO2; (xv) culturing a selected organism in said fermentation medium, whereby said carbon source is metabolized and an SCP-comprising broth is formed, at a given yield and given productivity of biomass production; (xvi) optionally, separating SCP from said SCP-comprising broth, whereby crude SCP and a residue are formed; (xvii) optionally washing said crude SCP, whereby washed SCP is formed; and (xviii) drying said SCP-comprising broth, said crude SCP or said washed SCP; wherein (a) the combined carbon content of said residual carbohydrate and said byproduct glycerol in said fermentation liquor is at least 3% of that in the carbohydrate of said glucose solution; and (b) said selected organism comprises an acetogenic organism.

According to an embodiment, said fermentation medium comprises at least two of said carbon sources. According to an embodiment, said fermentation medium comprises at least three of said carbon sources. According to an embodiment, said fermentation medium comprises at least four of said carbon sources. According to an embodiment, said fermentation medium comprises at least five of said carbon sources. According to an embodiment, said fermentation medium comprises at least six of said carbon sources. According to an embodiment, said fermentation medium comprises all seven carbon sources.

According to an embodiment, said culturing yeast specific duration is selected so that less than 95% by weight of the carbohydrates in said glucose solution is metabolized. According to an embodiment, said fermentation liquor comprises at least 10% by weight ethanol. According to an embodiment, said fermentation liquor comprises at least 0.5% by weight glycerol. According to an embodiment, said fermentation liquor residual carbohydrate comprises at least 0.5% by weight oligosaccharide.

According to an embodiment, said culturing selected organism is anaerobic. According to an embodiment, SCP generation yield is at least 15% by weight calculated on combined weight of carbohydrate and glycerol in said fermentation medium. According to an embodiment, SCP generation productivity is at least 0.5 g/L/hr. According to an embodiment, said selected organism further comprises an organism capable of metabolizing glycerol, oligosaccharides or a combination thereof.

According to an embodiment, said method further comprises adding an exogenous carbon source to said fermentation medium, wherein said exogenous carbon source is metabolized in said culturing selected organism.

According to an embodiment, said method further comprises lysing said crude SCP and/or said washed SCP.

According to an embodiment, said crude protein content of said crude SCP or said washed SCP on dry basis is at least 55% by weight. According to an embodiment, said said crude SCP or said washed SCP comprises at least 0.2% by weight butyric acid on dry basis. According to an embodiment, said crude SCP or said washed SCP comprises less than 5% by weight ash on dry basis.

Further provided is an integrated method for the production of ethanol and a single cell protein product, comprising (i) providing corn kernels, which kernels comprise germ, fiber, protein and starch; (ii) steeping said corn kernels, whereby steeped corn kernels and steep liquor are formed, which steep liquor comprises a first carbon source; (iii) separating said steeped kernels from said steep liquor, whereby separated steeped kernels and separated steep liquor are formed; (iv) optionally, concentrating said separated steep liquor by water removal therefrom, whereby concentrated steep liquor is formed; (v) mechanically separating germ from said separated steeped kernel, whereby separated germ is formed; (vi) mechanically separating fiber from said separated steeped kernel, whereby separated fiber is formed, which separated fiber comprises a second carbon source; (vii) optionally, blending separated fiber with separated steep liquor and/or with concentrated steep liquor, whereby a first blend is formed; (viii) separating starch from protein in said steeped kernel, whereby separated starch and a separated protein composition are formed, which separated protein composition comprises a third carbon source and which separated starch comprises a fourth carbon source; (ix) cooking and liquefying said separated starch, whereby liquefied starch is formed; (x) saccharifying said liquefied starch, whereby a glucose solution is formed; (xi) providing a fermentation medium comprising at least one carbon source selected from the group consisting of (a) said first carbon source; (b) said second carbon source; (c) said third carbon source; (d) said fourth carbon source; (e) liquefied starch; and (f) glucose solution, and optionally CO2; (xii) culturing in said medium yeast and a selected organism for a specific duration, whereby said carbohydrate is metabolized and carbon dioxide and a fermentation liquor are generated, which fermentation liquor comprises ethanol and single cell protein; (xiii) processing said fermentation liquor, which processing comprises distilling, separating solids and drying, whereby separated ethanol and a protein product are formed; wherein (a) said culturing specific duration is selected so that the carbon content of said separated ethanol is less than 64% of the carbon content of said fermentation medium carbohydrate; (b) said culturing specific duration is selected so that the carbon content of said single cell protein is at least 3% of the carbon content of said fermentation medium carbohydrate; and (c) said selected organism comprises an acetogenic organism.

Provided is an integrated method for the production of glucose and a single cell protein product, comprising (i) providing corn kernels, which kernels comprise germ, fiber, protein and starch; (ii) steeping said corn kernels, whereby steeped corn kernels and steep liquor are formed; (iii) separating said steeped kernels from said steep liquor, whereby separated steeped kernels and separated steep liquor are formed, which separated steep liquor comprises a first carbon source; (iv) optionally, concentrating said separated steep liquor by water removal therefrom, whereby concentrated steep liquor is formed; (v) mechanically separating germ from said separated steeped kernel, whereby separated germ is formed; (vi) mechanically separating fiber from said separated steeped kernel, whereby separated fiber is formed, which separated fiber comprises a second carbon source; (vii) optionally, blending separated fiber with separated steep liquor and/or with concentrated steep liquor, whereby a first blend is formed; (viii) separating starch from protein in said steeped kernel, whereby separated starch and a separated protein composition are formed, which separated protein composition comprises a third carbon source and which separated starch comprises a fourth carbon source; (ix) cooking and liquefying said separated starch, whereby liquefied starch is formed; (x) saccharifying said liquefied starch, whereby a glucose solution is formed; (xi) optionally isomerizing glucose of said solution into fructose; (xii) providing a fermentation medium comprising at least one carbon source selected from the group consisting of (a) said first carbon source; (b) said second carbon source; (c) said third carbon source; (d) said fourth carbon source; (e) liquefied starch; and (f) glucose solution; and optionally CO2; (xiii) culturing a selected organism in said fermentation medium, whereby said carbon source is metabolized and an SCP-comprising broth is formed, at a given yield and given productivity of biomass production; (xiv) optionally, separating SCP from said SCP-comprising broth, whereby crude SCP and a residue are formed; (xv) optionally washing said crude SCP, whereby washed SCP is formed; and (xvi) drying said SCP-comprising broth, said crude SCP or said washed SCP; wherein said selected organism comprises an acetogenic organism.

According to an embodiment, said fermentation medium comprises at least two of said carbon sources. According to an embodiment, said fermentation medium comprises at least three of said carbon sources. According to an embodiment, said fermentation medium comprises at least four of said carbon sources. According to an embodiment, said fermentation medium comprises at least five of said carbon sources. According to an embodiment, said fermentation medium comprises all said six carbon sources. According to an embodiment, said method further comprises adding an exogenous carbon source to said fermentation medium, wherein said exogenous carbon source is metabolized in said culturing selected organism.

According to an embodiment, said fermentation medium comprises at least 0.5% by weight oligosaccharide. According to an embodiment, said selected organism further comprises an organism capable of metabolizing glycerol, oligosaccharides or a combination thereof. According to an embodiment, said culturing selected organism is anaerobic.

According to an embodiment, SCP generation yield is at least 15% by weight calculated on combined carbon sources in said fermentation medium. According to an embodiment, SCP generation productivity is at least 0.5 g/L/hr.

According to an embodiment, said method further comprises lysing said crude SCP and/or said washed SCP.

According to an embodiment, crude protein content of said crude SCP or said washed SCP on dry basis is at least 55% by weight. According to an embodiment, said crude SCP or said washed SCP comprises at least 0.2% by weight butyric acid on dry basis. According to an embodiment, said crude SCP or said washed SCP comprises less than 5% by weight ash on dry basis.

Further provided is an integrated method for the production of water-soluble bioproduct and a single cell protein product, comprising (i) providing corn kernels, which kernels comprise germ, fiber, protein and starch; (ii) steeping said corn kernels, whereby steeped corn kernels and steep liquor are formed; (iii) separating said steeped kernels from said steep liquor, whereby separated steeped kernels and separated steep liquor are formed, which separated steep liquor comprises a first carbon source; (iv) optionally, concentrating said separated steep liquor by water removal therefrom, whereby concentrated steep liquor is formed; (v) mechanically separating germ from said separated steeped kernel, whereby separated germ is formed; (vi) mechanically separating fiber from said separated steeped kernel, whereby separated fiber is formed, which separated fiber comprises a second carbon source; (vii) optionally, blending separated fiber with separated steep liquor and/or with concentrated steep liquor, whereby a first blend is formed; (viii) separating starch from protein in said steeped kernel, whereby separated starch and a separated protein composition are formed, which separated protein composition comprises a third carbon source and which separated starch comprises a fourth carbon source; (ix) cooking and liquefying said separated starch, whereby liquefied starch is formed; (x) saccharifying said liquefied starch, whereby a glucose solution is formed; (xi) culturing a first organism in said glucose solution for a specific duration, whereby a fermentation liquor is formed, which fermentation liquor comprises a water soluble bioproduct; (xii) separating bioproduct from said fermentation liquor, whereby separated bioproduct and a liquid residue are formed, which residue comprises a fifth carbon source, and which fifth carbon source comprises residual carbohydrate and optionally byproduct glycerol; (xiii) optionally, blending separated fiber with separated steep liquor and/or with concentrated steep liquor and with said residue, whereby a second blend is formed; (xiv) providing a fermentation medium comprising at least one carbon source selected from the group consisting of (a) said first carbon source; (b) said second carbon source; (c) said third carbon source; (d) said fourth carbon source; (e) liquefied starch; (f) glucose solution, and (g) said fifth carbon source; and optionally CO2; (xv) culturing a selected second organism in said fermentation medium, whereby said carbon source is metabolized and an SCP-comprising broth is formed, at a given yield and given productivity of biomass production; (xvi) optionally, separating SCP from said SCP-comprising broth, whereby crude SCP and is formed; (xvii) optionally washing said crude SCP, whereby washed SCP is formed; and (xviii) drying said SCP-comprising broth, said crude SCP or said washed SCP; wherein the combined carbon content of said residual carbohydrate and said byproduct glycerol in said fermentation liquor is at least 3% of that in the carbohydrate of said glucose solution; and said selected second organism comprises an acetogenic organism.

According to an embodiment, said fermentation medium comprises at least two of said carbon sources. According to an embodiment, said fermentation medium comprises at least three of said carbon sources. According to an embodiment, said fermentation medium comprises at least four of said carbon sources. According to an embodiment, said fermentation medium comprises at least five of said carbon sources. According to an embodiment, said fermentation medium comprises at least six of said carbon sources. According to an embodiment, said fermentation medium comprises all seven carbon sources.

According to an embodiment, said method further comprises adding an exogenous carbon source to said fermentation medium, wherein said exogenous carbon source is metabolized in said culturing selected organism.

According to an embodiment, said culturing first organism specific duration is selected so that less than 95% by weight of the carbohydrates in said glucose solution is metabolized. According to an embodiment, said fermentation liquor comprises at least 10% by weight bioproduct. According to an embodiment, said fermentation liquor comprises at least 0.5% by weight glycerol. According to an embodiment, said fermentation liquor residual carbohydrate comprises at least 0.5% by weight oligosaccharide.

According to an embodiment, said selected second organism further comprises an organism capable of metabolizing glycerol, oligosaccharides or a combination thereof. According to an embodiment, said culturing selected second organism is anaerobic.

According to an embodiment, SCP generation yield is at least 15% by weight calculated on combined weight of carbohydrate and glycerol in said fermentation medium. According to an embodiment, SCP generation productivity is at least 0.5 g/L/hr.

According to an embodiment, crude protein content of said crude SCP or said washed SCP on dry basis is at least 55% by weight. According to an embodiment, said crude SCP or said washed SCP comprises at least 0.2% by weight butyric acid on dry basis. According to an embodiment, said crude SCP or said washed SCP comprises less than 5% by weight ash on dry basis.

According to an embodiment, said method further comprising lysing said crude SCP and/or said washed SCP.

DETAILED DESCRIPTION OF THE INVENTION

As used herein SCP refers to Single-Cell Protein

Unless indicated otherwise, percent is weight percent and ratio is weight/weight ratio. The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

The present invention will now be described by reference to more detailed embodiments. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Additional advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

Provided is an integrated method for the production of ethanol and a single cell protein product, comprising (i) providing corn kernels, which kernels comprise germ, fiber, protein and starch; (ii) steeping said corn kernels, whereby steeped corn kernels and steep liquor are formed; (iii) separating said steeped kernels from said steep liquor, whereby separated steeped kernels and separated steep liquor are formed, which separated steep liquor comprises a first carbon source; (iv) optionally, concentrating said separated steep liquor by water removal therefrom, whereby concentrated steep liquor is formed; (v) mechanically separating germ from said separated steeped kernel, whereby separated germ is formed; (vi) mechanically separating fiber from said separated steeped kernel, whereby separated fiber is formed, which separated fiber comprises a second carbon source; (vii) optionally, blending separated fiber with separated steep liquor and/or with concentrated steep liquor, whereby a first blend is formed; (viii) separating starch from protein in said steeped kernel, whereby separated starch and a separated protein composition are formed, which separated protein composition comprises a third carbon source and which separated starch comprises a fourth carbon source; (ix) cooking and liquefying said separated starch, whereby liquefied starch is formed; (x) saccharifying said liquefied starch to a glucose solution; (xi) culturing yeast in said glucose solution for a specific duration, whereby $CO_2$ and an ethanol comprising fermentation liquor are formed; (xii) distilling ethanol from said fermentation liquor, whereby separated ethanol and stillage are formed, which stillage comprising a fifth carbon source, which fifth carbon source comprises residual carbohydrate and optionally byproduct glycerol, (xiii) optionally, blending separated fiber with separated steep liquor and/or with concentrated steep liquor and with said stillage, whereby a second blend is formed; (xiv) providing a fermentation medium comprising at least one carbon source selected from the group consisting of (a) said first carbon source; (b) said second carbon source; (c) said third carbon source; (d) said fourth carbon source; (e) liquefied starch; (f) glucose solution, and (g) said fifth carbon source; and optionally $CO_2$; (xv) culturing a selected organism in said fermentation medium, whereby said carbon source is metabolized and an SCP-comprising broth is formed, at a given yield and given productivity of biomass production; (xvi) optionally, separating SCP from said SCP-comprising broth, whereby crude SCP and a residue are formed; (xvii) optionally washing said crude SCP, whereby washed SCP is formed; and (xviii) drying said SCP-comprising broth, said crude SCP or said washed SCP; wherein (a) the combined carbon content of said residual carbohydrate and said byproduct glycerol in said fermentation liquor is at least 3% of that in the carbohydrate of said glucose solution; and (b) said selected organism comprises an acetogenic organism.

According to an embodiment, the method comprises providing conventional corn kernels. Corn kernels are composed of the pericarp (coat), the germ and the endosperm and typically contain, on a dry basis, about 4% corn oil (in the germ), about 12% fiber (in the pericarp) 70% starch and 10% protein (in the endosperm, where starch granules are found in a protein matrix). According to an embodiment, the method comprises steps directed to fractionating the corn kernel into a fiber fraction, a germ fraction, a protein fraction and a starch fraction.

According to an embodiment, the method comprises steeping said corn kernels, whereby steeped corn kernels and steep liquor are formed. According to an embodiment, corn kernels are steeped in a solution containing SO2 and lactic acid at about 50° C., which leads to softening and to loosening of the pericarp protein matrix. During steeping, sugars, peptides and other components diffuse out of the kernels. According to an embodiment, after about 40 hours, steeped kernels are separated from the steep liquor, whereby separated steeped kernels and separated steep liquor are formed, which separated steep liquor comprises a first carbon source, including carbohydrates, such as starch, oligosaccharides, disaccharides and monosaccharides, such as glucose. According to an embodiment, the separated steep liquor is treated with phytase enzymes. According to an embodiment, the separated steep liquor is concentrated by water evaporation, e.g. in multiple stage evaporators.

According to an embodiment, the method comprises mechanically separating germ from said separated steeped kernel, whereby separated germ is formed and optionally extracting corn oil from said separated germ.

According to an embodiment, the method further comprises mechanically separating fiber from said separated steeped kernel, whereby separated fiber is formed, which separated fiber comprises a second carbon source. According to an embodiment, said separated fiber comprises starch due to imperfect separation. According to an embodiment, the method further comprises chemically and/or enzymatically-catalyzed hydrolysis of separated fiber, whereby hexoses (e.g. glucose) and pentoses (e.g. xylose) are formed. According to an embodiment, the method further comprises blending separated fiber with separated steep liquor and/or with concentrated steep liquor to form a first blend.

According to an embodiment, the method further comprises separating starch from protein in said steeped kernel, whereby separated starch and a separated protein composition are formed, which separated protein composition comprises a third carbon source and which separated starch comprises a fourth carbon source. According to an embodiment, said separated protein composition, also referred to as gluten mill, comprises starch due to imperfect separation.

According to an embodiment, the method further comprises cooking and liquefying said separated starch, whereby liquefied starch is formed and saccharifying said liquefied starch to a glucose solution. According to an embodiment, cooking and saccharifying use commercial enzymes.

According to an embodiment said method comprises culturing yeast in said glucose solution for a specific duration, whereby a fraction of the carbohydrate in said glucose solution is metabolized and carbon dioxide and a fermentation liquor are generated, which fermentation liquor comprises ethanol, residual carbohydrate, and optionally byproduct glycerol.

According to current commercial practices, ethanol production is conducted at conditions wherein metabolizing of fermentation liquor carbohydrates approaches the theoretical yields, which in turn leads to nearly theoretical yields on ethanol production. This, however, comes at a cost in providing said fermentation medium, in metabolizing of the carbohydrates and/or in ethanol recovery from the formed fermentation liquor. Thus, yeast might be less efficient in metabolizing oligosaccharides, so that optimizing metabolizing yields may require nearly complete saccharification of starch into glucose in providing the fermentation medium.

Improving starch hydrolysis comes at the cost of increased enzyme consumptions and/or increased capital and energy cost in the hydrolysis step. Alternatively or additionally, higher fermentation yields can be reached by extending the duration of culturing, which comes at the cost of increased fermentation capital cost. Additionally, at high fermentation medium glucose concentration, yeast tends to convert a fraction of the carbohydrate into glycerol, rather than to ethanol. Glucose concentration in the fermentation medium can be kept relatively low, but that results in lower concentration of ethanol in the formed fermentation liquor. One result is the need for larger fermenters, i.e. high fermentation capital yield, and higher capital and energy cost in recovering the formed ethanol.

Contrary to said current commercial practices, according to an embodiment, the parameters of the method of the present invention, are selected to lead to lower costs of providing the medium, lower costs of fermenting the carbohydrates to ethanol and lower costs of ethanol recovery, even if compromising on the yield of fermenting carbohydrates to ethanol. Hence, according to an embodiment, said culturing yeast specific duration is selected so that less than 95% by weight of the glucose in said glucose solution is metabolized, less than 94%, less than 93%, less than 92%, less than 91%, less than 90%, less than 89%%, or less than 88%. According to an embodiment, said formed fermentation liquor comprises, in addition to ethanol, also residual carbohydrate and/or byproduct glycerol. According to an embodiment, said residual carbohydrate comprises an oligosaccharide selected from the group consisting of disaccharides, trisacchrides, higher molecular weight oligomers and combinations thereof. According to an embodiment, the combined carbon content of said residual carbohydrate and said byproduct glycerol in said fermentation liquor is at least 3% of that in the glucose of said glucose solution, at least 4%, at least 5%, at least 6%, at least 7%, at least 8%, at least 9%, at least 10%, at least 11%, or at least 12%. The carbon content can be calculated via the molecular formula, e.g. the carbon contents of a solution containing 12% glucose and one containing 2% glycerol are 12×72/180 and 2×36/92, respectively. According to an embodiment, said fermentation liquor comprises at least 10% ethanol, at least 12%, at least 14%, at least 16% or at least 17%. According to an embodiment said fermentation liquor comprises at least 0.5% glycerol, at least 0.6%, at least 0.7%, at least 0.8%, at least 0.9%, at least 1%, at least 1.1%, or at least 1.2%. Additionally or alternatively, according to an embodiment said fermentation liquor residual carbohydrate comprises at least 0.5% oligosaccharide, at least 0.6%, at least 0.7%, at least 0.8%, at least 0.9%, at least 1%, at least 1.1%, or at least 1.2%.

According to an embodiment, the method further comprises distilling ethanol from said fermentation liquor, whereby separated ethanol and stillage are formed, which stillage comprises a fifth carbon source, which fifth carbon source comprises residual carbohydrate and optionally byproduct glycerol. According to an embodiment, the method further comprises blending separated fiber with separated steep liquor and/or with concentrated steep liquor and with at least a fraction of said stillage, whereby a second blend is formed, which second blend is also referred to as gluten feed.

According to an embodiment, the method further comprises providing a fermentation medium comprising at least one carbon source selected from the group consisting of (a) said first carbon source; (b) said second carbon source; (c) said third carbon source; (d) said fourth carbon source; (e) liquefied starch; (f) glucose solution, or (g) said fifth carbon source; and optionally $CO_2$. According to an embodiment, said fermentation medium comprising at least at least two of said carbon sources, at least three of said carbon sources, at least four of said carbon sources, at least five of said carbon sources, at least six of said carbon sources or all seven carbon sources.

According to an embodiment, said fermentation medium comprises said separated steep liquor and/or said concentrated steep liquor. According to an embodiment, said fermentation medium comprises phytase-treated separated steep liquor and/or phytase-treated concentrated steep liquor.

According to an embodiment, said fermentation medium comprises mechanically separated fiber. According to an embodiment, said fermentation medium comprises chemically and/or enzymatically-catalyzed hydrolyzed separated fiber. According to an embodiment, said fermentation medium comprises glucose and xylose.

According to an embodiment, said fermentation medium comprises a protein composition mechanically separated from starch in said steeped kernel. Said separated protein composition is also referred to as gluten meal. According to an embodiment, said protein composition comprises imperfectly separated starch.

According to an embodiment, said fermentation medium comprises starch mechanically separated from protein in said steeped kernel. According to an embodiment, said fermentation medium comprises liquefied starch. According to an embodiment, said fermentation medium comprises a glucose solution formed on saccharifying starch and/or on saccharifying liquefied starch.

According to an embodiment, said fermentation medium comprises stillage formed on distilling ethanol from said fermentation liquor. According to an embodiment, said stillage comprises residual carbohydrate and optionally byproduct glycerol. According to an embodiment, said stillage residual carbohydrate comprises oligosaccharides. According to an embodiment, the combined carbon content of said residual carbohydrate and said byproduct glycerol in said fermentation liquor is at least 3% of that in the carbohydrate of said glucose solution.

According to an embodiment, said method comprises adding an exogenous carbon source to said syrup, sweet syrup or modified sweet syrup, wherein said exogenous carbon source is metabolized in said culturing selected organism.

According to an embodiment, said fermentation medium comprises culturing a selected organism in said fermentation medium, whereby said carbon source is metabolized and an SCP-comprising broth is formed, at a given yield and given productivity of biomass production. According to an embodiment, said selected organism comprises an acetogenic organism. According to an embodiment, said acetogenic organism is selected from the group consisting of *Butyribacterium methylotrophicum, Blautia product, Clostridium drakei, Clostridium magnum, Clostridium scatologenes, Clostridium ljungdahlii, Clostridium autoethanogenum, Clostridium aceticum, Clostridium ragsdalei, Clostridium carboxidivorans, Eubacterium aggregans, Eubacterium limosum, Acetobacterium woodii, Oxobacter pfennigii, Treponema azotonutricium, Sporosoma ovata, Sporosoma termitida*, and *Terriporobacter glycolicus*. According to an embodiment, said selected organism further comprises an organism selected from the group consisting of organisms capable of metabolizing glycerol, oligosaccharides or a combination thereof. According to an embodiment, said organism capable of metabolizing glycerol, oligosaccharides or a combination thereof is selected from the group consisting of *Clostridium pasteurianum, Clostridium tyrobutyricum, Clostridium butyricum, Clostridium acetobutylicum, Clostridium beijerinckii, Clostridium sporogenes, Clostridium saccharoperbutylacetonicum,* and *Clostridium saccharobutylicum.*

According to an embodiment, said culturing selected organism is anaerobic.

According to an embodiment, said selected organism further comprises an organism capable of metabolizing glycerol, oligosaccharides or a combination thereof.

According to an embodiment, biomass generation yield is at least 15% weight calculated on combined weight of carbohydrate and glycerol, at least 20%, at least 25%, at least 30% or at least 35%. Biomass generation yield is calculated according to the ratio between formed biomass on dry basis and the combined weight of carbohydrate and glycerol in said fermentation liquor and/or in said treated broth. According to an embodiment, biomass generation yield is at least 15% weight calculated on combined weight of carbohydrate and glycerol, at least 20%, at least 25%, at least 30% or at least 35%.

According to an embodiment, biomass generation productivity is at least 0.5 g/L/hr, at least 0.6 g/L/hr, at least 0.7 g/L/hr, at least 0.8 g/L/hr, at least 0.9 g/L/hr, or at least 1 g/L/hr.

According to an embodiment, said culturing selected organism generates, in addition to biomass, at least one metabolite selected from the group consisting of acetic acid, butyric acid, lactic acid, formic acid, 1,3-propanediol, n-butanol, ethanol, acetoin, and 2,3-butanediol. According to an embodiment, the concentration of butyric acid in said SCP-comprising broth is in the range between 0.5% and 15%.

According to an embodiment, said method comprises separating SCP from said SCP-comprising broth, whereby crude SCP and a residue are formed. According to an embodiment, said method comprises washing said crude SCP, whereby washed SCP is formed. According to an embodiment, said method comprises drying said SCP-comprising broth, said crude SCP or said washed SCP. According to an embodiment, said method comprises lysing said crude SCP, said washed SCP, said dried crude SCP and/or said dried washed SCP.

According to an embodiment, the crude protein content of said crude SCP or said washed SCP, on dry basis, is at least 55% by weight, at least 60%, at least 65% or at least 70%. According to an embodiment, said crude SCP or said washed SCP comprise, on dry basis, at least 0.2% by weight butyric acid, at least 0.4%, at least 0.6%, at least 0.8% or at least 1%. According to an embodiment, said crude SCP or said washed SCP comprise, on dry basis, less than 5% by weight ash, less than 4%, less than 3% or less than 2%.

According to an embodiment, said crude SCP or said washed SCP, comprises on dry basis between 62% by weight and 75% by weight crude protein, at least 0.2% by weight butyric acid and at least three of, at least four of or all five of (i) between 5.5% by weight and 6.9% by weight lysine; (ii) between 2.1% by weight and 3.5% by weight methionine; (iii) between 3.1% by weight and 4.4% by weight threonine; (iv) between 2.0% by weight and 3.3% by weight tryptophan and (v) between 2.5% by weight and 4.5% by weight crude fat. According to an embodiment said dried crude SCP or said dried washed SCP comprises on dry basis between 0.2% by weight and 2.0% by weight butyric acid. According to an embodiment said dried crude SCP or said dried washed SCP comprises on dry basis between 4% by weight and 8% by weight ash.

Figure 1:
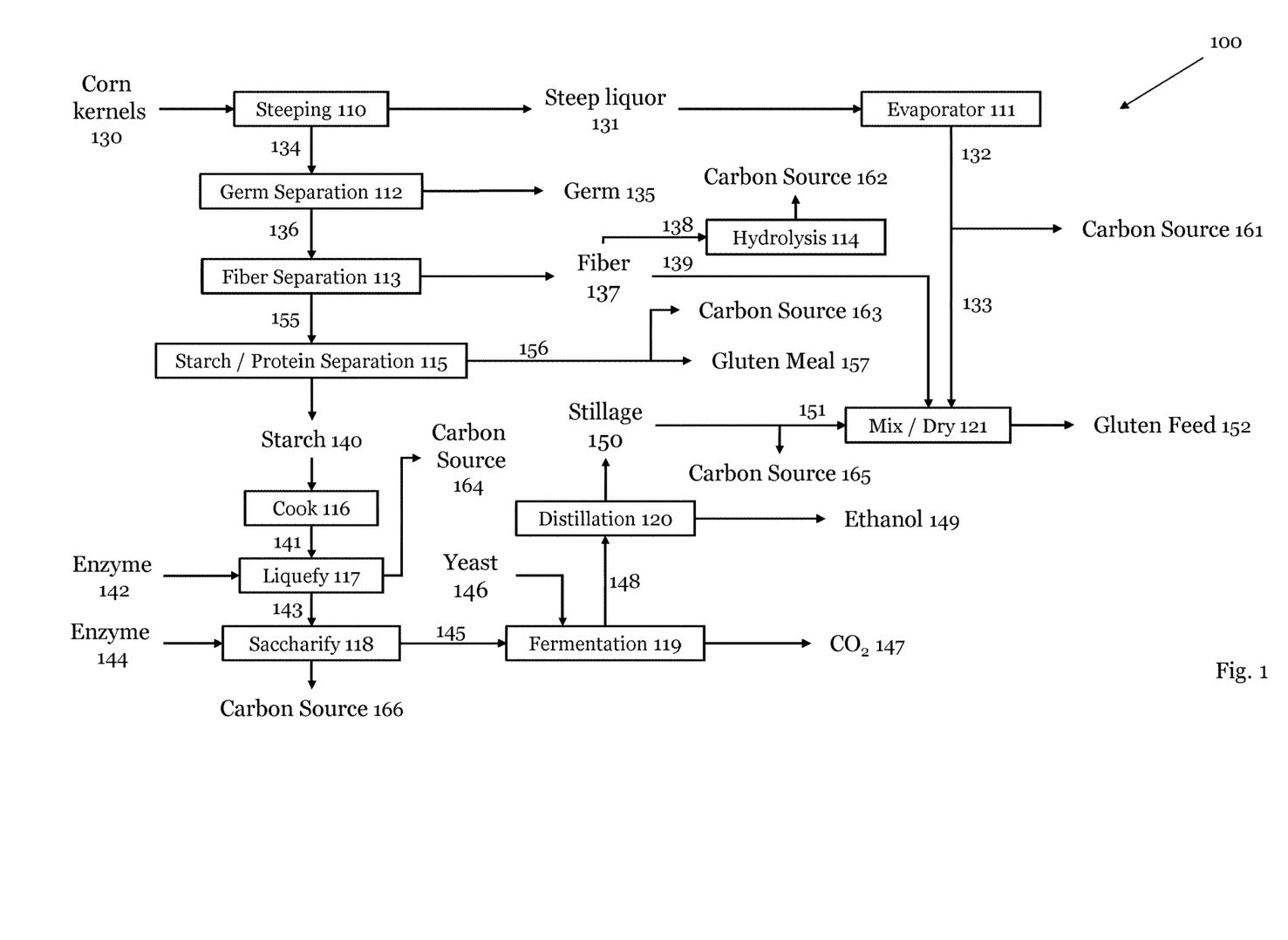
FIG. 1 shows a first exemplary embodiment of the method that includes the production of ethanol.
Figure 2:
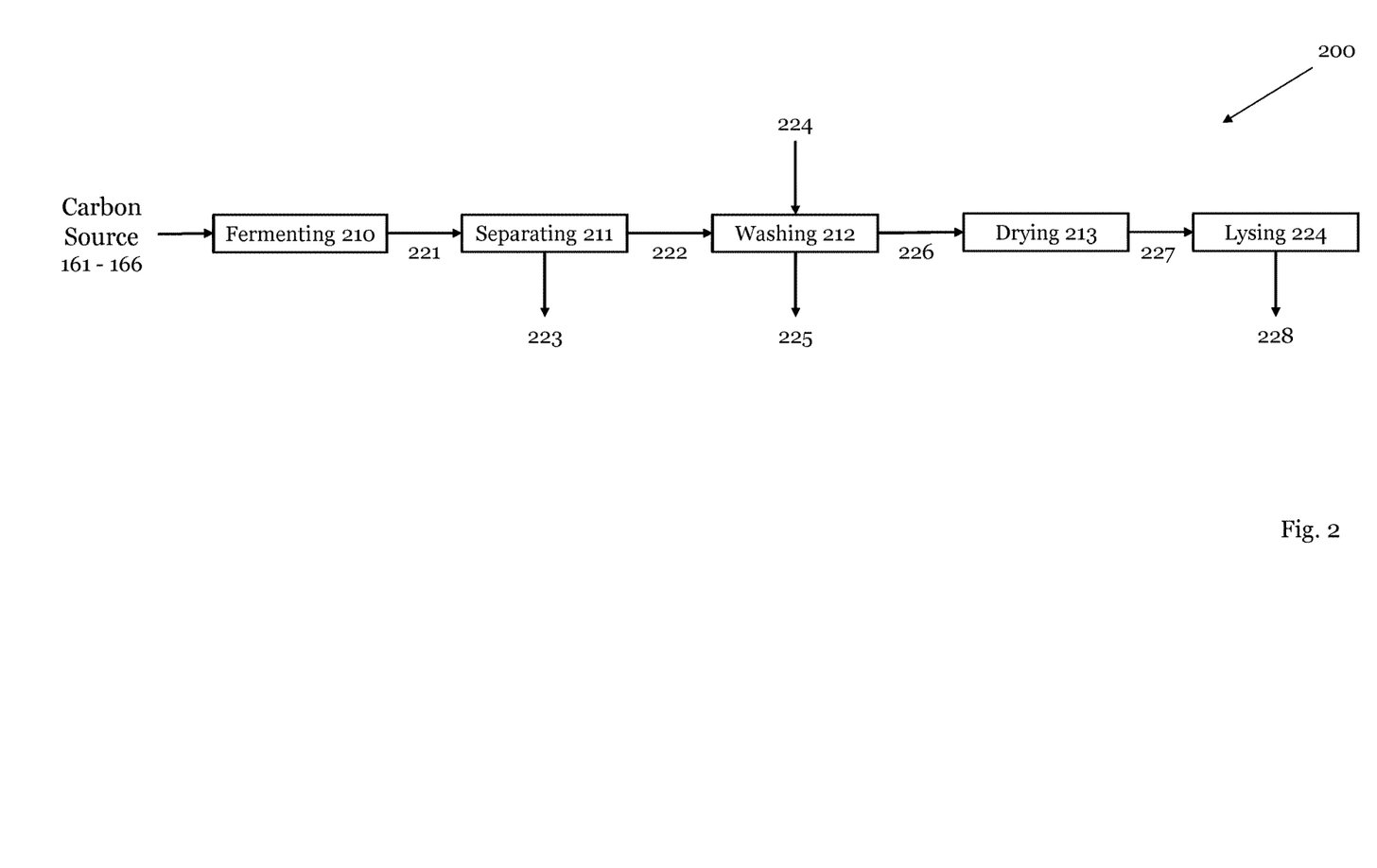
FIG. 2 shows a second exemplary embodiment of the method that includes the production of single cell protein product.

An exemplary embodiment of the method is presented in FIGS. 1 and 2.

As shown in FIG. 1, corn kernels (130) are introduced into a steeping tank (110) for about 40 hours, whereby steeped corn kernels (134) and steep liquor (131) are formed. The steep liquor is evaporated in evaporator (111) to form concentrated steep liquor (132). A fraction of said concentrated steep liquor, comprising a first carbon source (161), is sent to SCP production. Another fraction of the concentrated steep liquor (133) is sent to gluten feed production (121).

Steeped kernels (134) are mechanically treated in (112) for separating germ therefrom. The separated germ (135) is optionally treated in an extractor (not shown in the figure) for the production of corn oil.

The degermed steeped kernels (136) are mechanically treated in (113) for separating fiber (137) therefrom. A fraction of the fiber (139) is sent to gluten feed production (121). Another fraction of the fiber (138) is hydrolyzed in a hydrolysis reactor (114), whereby a hydrolysate is formed. Said hydrolysate (162) comprises the second carbon source and is sent to SCP production.

After separation of the germ and fiber, the steeped kernels (155) are mechanically treated for starch/protein separation in (115). A separated protein composition (156) is formed. A fraction of said protein composition, comprising the third carbon source (163), is sent to SCP production. Another fraction of said protein composition is used as gluten meal (157) in animal feed.

The separated starch (140) is cooked in cooking reactor (116) to form cooked starch (141). The cooked starch is treated with enzymes (142) in liquefying reactor (117), whereby liquefied starch is formed. A fraction of the liquefied starch, comprising the fourth carbon source (164), is sent to SCP production. Another fraction of the liquefied starch (143) is treated with enzymes (144) in a saccharifying reactor (118) to form a glucose solution. A fraction of said glucose solution (166) is sent to SCP production.

Another fraction of said glucose solution (145) is fermented for a specific duration in fermenter (119) using yeast (146). $CO_2$ (147) and an ethanol comprising fermentation liquor (148) are formed. The fermentation liquor is treated in distillation columns (120), whereby separated ethanol (149) and stillage (150) are formed. A fraction of said stillage, comprising a fifth carbon source (165) is sent to SCP production. Another fraction of the stillage (151) is sent to gluten feed production (121), where it is mixed with the fraction of the concentrated steep liquor (133) and the fraction of the fiber (139) to form gluten feed (152).

As shown in FIG. 2, one or more of the carbon sources of (161)-(166) are introduced into fermenter (210) to provide a fermentation medium. A selected organism is cultured in said fermentation medium, whereby said carbon source are metabolized and an SCP-comprising broth (221) is formed. SCP is separated in a centrifuge (211), forming crude SCP (222) and a residue (223). In a washing unit (212), crude SCP is washed with water (224), forming wash water (225) and washed SCP (226). The washed SCP is dried in a drier (213) to form washed and dried SCP (227). The washed and dried SCP is lysed in (214) to form lysed SCP (228).

Further provided is an integrated method for the production of ethanol and a single cell protein product, comprising (i) providing corn kernels, which kernels comprise germ, fiber, protein and starch; (ii) steeping said corn kernels, whereby steeped corn kernels and steep liquor are formed, which steep liquor comprises a first carbon source; (iii)

separating said steeped kernels from said steep liquor, whereby separated steeped kernels and separated steep liquor are formed; (iv) optionally, concentrating said separated steep liquor by water removal therefrom, whereby concentrated steep liquor is formed; (v) mechanically separating germ from said separated steeped kernel, whereby separated germ is formed; (vi) mechanically separating fiber from said separated steeped kernel, whereby separated fiber is formed, which separated fiber comprises a second carbon source; (vii) optionally, blending separated fiber with separated steep liquor and/or with concentrated steep liquor, whereby a first blend is formed; (viii) separating starch from protein in said steeped kernel, whereby separated starch and a separated protein composition are formed, which separated protein composition comprises a third carbon source and which separated starch comprises a fourth carbon source; (ix) cooking and liquefying said separated starch, whereby liquefied starch is formed; (x) saccharifying said liquefied starch, whereby a glucose solution is formed; (xi) providing a fermentation medium comprising at least one carbon source selected from the group consisting of (a) said first carbon source; (b) said second carbon source; (c) said third carbon source; (d) said fourth carbon source; (e) liquefied starch; and (f) glucose solution, and optionally $CO_2$; (xii) culturing in said medium yeast and a selected organism for a specific duration, whereby said carbohydrate is metabolized and carbon dioxide and a fermentation liquor are generated, which fermentation liquor comprises ethanol and single cell protein; (xiii) processing said fermentation liquor, which processing comprises distilling, separating solids and drying, whereby separated ethanol and a protein product are formed; wherein (a) said culturing specific duration is selected so that the carbon content of said separated ethanol is less third than 64% of the carbon content of said fermentation medium carbohydrate; (b) said culturing specific duration is selected so that the carbon content of said single cell protein is at least 3% of the carbon content of said fermentation medium carbohydrate; and (c) said selected organism comprises an acetogenic organism.

Provided is an integrated method for the production of glucose and a single cell protein product, comprising (i) providing corn kernels, which kernels comprise germ, fiber, protein and starch; (ii) steeping said corn kernels, whereby steeped corn kernels and steep liquor are formed; (iii) separating said steeped kernels from said steep liquor, whereby separated steeped kernels and separated steep liquor are formed, which separated steep liquor comprises a first carbon source; (iv) optionally, concentrating said separated steep liquor by water removal therefrom, whereby concentrated steep liquor is formed; (v) mechanically separating germ from said separated steeped kernel, whereby separated germ is formed; (vi) mechanically separating fiber from said separated steeped kernel, whereby separated fiber is formed, which separated fiber comprises a second carbon source; (vii) optionally, blending separated fiber with separated steep liquor and/or with concentrated steep liquor, whereby a first blend is formed; (viii) separating starch from protein in said steeped kernel, whereby separated starch and a separated protein composition are formed, which separated protein composition comprises a third carbon source and which separated starch comprises a fourth carbon source; (ix) cooking and liquefying said separated starch, whereby liquefied starch is formed; (x) saccharifying said liquefied starch, whereby a glucose solution is formed; (xi) optionally isomerizing glucose of said solution into fructose; (xii) providing a fermentation medium comprising at least one carbon source selected from the group consisting of (a) said first carbon source; (b) said second carbon source; (c) said third carbon source; (d) said fourth carbon source; (e) liquefied starch; and (f) glucose solution; and optionally $CO_2$; (xiii) culturing a selected organism in said fermentation medium, whereby said carbon source is metabolized and an SCP-comprising broth is formed, at a given yield and given productivity of biomass production; (xiv) optionally, separating SCP from said SCP-comprising broth, whereby crude SCP and a residue are formed; (xv) optionally washing said crude SCP, whereby washed SCP is formed; and (xvi) drying said SCP-comprising broth, said crude SCP or said washed SCP; wherein said selected organism comprises an acetogenic organism.

According to an embodiment, said fermentation medium comprises at least two of said carbon sources. According to an embodiment, said fermentation medium comprises at least three of said carbon sources. According to an embodiment, said fermentation medium comprises at least four of said carbon sources. According to an embodiment, said fermentation medium comprises at least five of said carbon sources. According to an embodiment, said fermentation medium comprises all said six carbon sources. According to an embodiment, said method further comprises adding an exogenous carbon source to said fermentation medium, wherein said exogenous carbon source is metabolized in said culturing selected organism.

According to an embodiment, said fermentation medium comprises at least 0.5% by weight oligosaccharide. According to an embodiment, said selected organism further comprises an organism capable of metabolizing glycerol, oligosaccharides or a combination thereof. According to an embodiment, said culturing selected organism is anaerobic.

According to an embodiment, SCP generation yield is at least 15% by weight calculated on combined carbon sources in said fermentation medium. According to an embodiment, SCP generation productivity is at least 0.5 g/L/hr.

According to an embodiment, said method further comprises lysing said crude SCP and/or said washed SCP.

According to an embodiment, crude protein content of said crude SCP or said washed SCP on dry basis is at least 55% by weight. According to an embodiment, said crude SCP or said washed SCP comprises at least 0.2% by weight butyric acid on dry basis. According to an embodiment, said crude SCP or said washed SCP comprises less than 5% by weight ash on dry basis.

Further provided is an integrated method for the production of water-soluble bioproduct and a single cell protein product, comprising (i) providing corn kernels, which kernels comprise germ, fiber, protein and starch; (ii) steeping said corn kernels, whereby steeped corn kernels and steep liquor are formed; (iii) separating said steeped kernels from said steep liquor, whereby separated steeped kernels and separated steep liquor are formed, which separated steep liquor comprises a first carbon source; (iv) optionally, concentrating said separated steep liquor by water removal therefrom, whereby concentrated steep liquor is formed; (v) mechanically separating germ from said separated steeped kernel, whereby separated germ is formed; (vi) mechanically separating fiber from said separated steeped kernel, whereby separated fiber is formed, which separated fiber comprises a second carbon source; (vii) optionally, blending separated fiber with separated steep liquor and/or with concentrated steep liquor, whereby a first blend is formed; (viii) separating starch from protein in said steeped kernel, whereby separated starch and a separated protein composition are formed, which separated protein composition comprises a third carbon source and which separated starch comprises a fourth carbon source; (ix) cooking and liquefying said separated starch, whereby liquefied starch is formed; (x) saccharifying said liquefied starch, whereby a glucose solution is formed; (xi) culturing a first organism in said glucose solution for a specific duration, whereby a fermentation liquor is formed, which fermentation liquor comprises a water soluble bioproduct; (xii) separating bioproduct from said fermentation liquor, whereby separated bioproduct and a liquid residue are formed, which residue comprises a fifth carbon source, and which fifth carbon source comprises residual carbohydrate and optionally byproduct glycerol; (xiii) optionally, blending separated fiber with separated steep liquor and/or with concentrated steep liquor and with said residue, whereby a second blend is formed; (xiv) providing a fermentation medium comprising at least one carbon source selected from the group consisting of (a) said first carbon source; (b) said second carbon source; (c) said third carbon source; (d) said fourth carbon source; (e) liquefied starch; (f) glucose solution, and (g) said fifth carbon source; and optionally CO2; (xv) culturing a selected second organism in said fermentation medium, whereby said carbon source is metabolized and an SCP-comprising broth is formed, at a given yield and given productivity of biomass production; (xvi) optionally, separating SCP from said SCP-comprising broth, whereby crude SCP and is formed; (xvii) optionally washing said crude SCP, whereby washed SCP is formed; and (xviii) drying said SCP-comprising broth, said crude SCP or said washed SCP; wherein the combined carbon content of said residual carbohydrate and said byproduct glycerol in said fermentation liquor is at least 3% of that in the carbohydrate of said glucose solution; and said selected second organism comprises an acetogenic organism.

According to an embodiment, said fermentation medium comprises at least two of said carbon sources. According to an embodiment, said fermentation medium comprises at least three of said carbon sources. According to an embodiment, said fermentation medium comprises at least four of said carbon sources. According to an embodiment, said fermentation medium comprises at least five of said carbon sources. According to an embodiment, said fermentation medium comprises at least six of said carbon sources. According to an embodiment, said fermentation medium comprises all seven carbon sources.

According to an embodiment, said method further comprises adding an exogenous carbon source to said fermentation medium, wherein said exogenous carbon source is metabolized in said culturing selected organism.

According to an embodiment, said culturing first organism specific duration is selected so that less than 95% by weight of the carbohydrates in said glucose solution is metabolized. According to an embodiment, said fermentation liquor comprises at least 10% by weight bioproduct. According to an embodiment, said fermentation liquor comprises at least 0.5% by weight glycerol. According to an embodiment, said fermentation liquor residual carbohydrate comprises at least 0.5% by weight oligosaccharide.

According to an embodiment, said selected second organism further comprises an organism capable of metabolizing glycerol, oligosaccharides or a combination thereof. According to an embodiment, said culturing selected second organism is anaerobic.

According to an embodiment, SCP generation yield is at least 15% by weight calculated on combined weight of carbohydrate and glycerol in said fermentation medium. According to an embodiment, SCP generation productivity is at least 0.5 g/L/hr.

According to an embodiment, crude protein content of said crude SCP or said washed SCP on dry basis is at least 55% by weight. According to an embodiment, said crude SCP or said washed SCP comprises at least 0.2% by weight butyric acid on dry basis. According to an embodiment, said crude SCP or said washed SCP comprises less than 5% by weight ash on dry basis.

According to an embodiment, said method further comprising lysing said crude SCP and/or said washed SCP.

EXAMPLES

Example 1: Production of SCP-Comprising Broth from Wet-Mill Glucose Solution

Wet-mill processing creates a glucose solution from corn. Briefly, corn kernels are first steeped and then the germ, fiber, and protein fractions are removed, leaving a separated starch stream. This starch stream is then cooked and liquified and finally saccharified into a glucose solution. This glucose solution can be used as the primary carbon source in a fermentation for ethanol from yeast or in a fermentation to generate single cell protein (SCP).

For SCP production, the glucose solution is mixed with nutrients before fermentation. The nutrients can include, at a final concentration, $KH_2PO_4$ at 4.5 g/L, $MgSO_4.7H_2O$ at 0.5 g/L, $FeSO_4.7H_2O$ at 0.03 g/L, trace elements at 20 mL/L and vitamins at 20 mL/L. The trace elements solution is 2 g/L nitrilotriacetic acid, 1 g/L $MnSO_4.H_2O$, 0.8 g/L $Fe(SO_4)_2(NH_4)_2.6H_2O$, 0.2 g/L $CoCl_2.6H_2O$, 0.2 mg/L $ZnSO_4.6H_2O$, 0.02 g/L $CuCl_2.2H_2O$, 0.02 g/L $NiCl_2.6H_2O$, 0.02 g/L $Na_2MoO_4.2H_2O$, 0.02 g/L $Na_2SeO_4$, and 0.02 g/L $Na_2WO_4$. The vitamin solution is 2 mg/L biotin, 2 mg/L folic acid, 10 mg/L pyridoxine-HCl, 5 mg/L thiamine-HCl, 5 mg/L riboflavin, 5 mg/L nicotinic acid, 5 mg/L calcium D-(+)-pantothenate, 0.1 mg/L vitamin b12, 5 mg/L p-aminobenzoic acid, and 5 mg/L thioctic acid. Additionally, antifoam is added at 0.1 mL/L. The fermenter is inoculated with a culture of equal parts *Clostridium tryobutyricum* and *Butyribacterium methylotrophicum*, an acetogenic bacterium. The fermenter is sparged with $CO_2$ at <25 mL/min, controlled at 35-37° C., and pH bottom controlled at 6.5 with 8M NaOH. The fermentation is run to generate an SCP-comprising broth. The productivity of SCP production is at least 0.5 g/L/hr and the final yield is at least 15 wt % (g SCP/g glucose). The whole SCP-comprising broth is dried to generate a protein-rich product.

Example 2: Production of Crude SCP from Wet-Mill Glucose Solution

The SCP from the SCP-comprising broth in Example 1 is separated from the broth by centrifugation or other liquid/solid separation method to generate a crude SCP. This SCP is dried to generate a crude SCP product. This crude SCP is at least 55 wt % crude protein and less than 5 wt % ash. It also contains at least 0.2 wt % butyric acid.

Example 3: Production of Washed SCP from Wet-Mill Glucose Solution

The undried crude SCP from Example 3 is washed at least once with water to generate a washed SCP. This washed SCP is dried to generate a washed SCP product. This washed SCP is at least 55 wt % crude protein and less than 5 wt % ash. It also contains at least 0.2 wt % butyric acid.

Example 4: Production of SCP-Comprising Broth from Wet-Mill Glucose Solution and at Least One Other Source To the SCP fermentation in Example 1, at least one additional carbon source is added. These sources include: corn steep liquor, corn fiber, a blend of corn steep liquor and corn fiber, corn protein, corn starch, stillage from a wet-mill ethanol fermentation, a blend of corn steep liquor and ethanol stillage, or liquified corn starch. The same nutrients and micronutrients can be added to the fermentation. The fermenter is inoculated and run as stated in Example 1, and an SCP-comprising broth is generated. SCP production is at least 0.5 g/L/hr and the yield is at least 15 wt %. The SCP-comprising broth is dried to generate a protein-rich product.

Example 5: Production of Crude SCP from Wet-Mill Glucose Solution and at Least One Other Source The SCP from the SCP-comprising broth in Example 4 is separated from the broth by centrifugation or other liquid/solid separation method to generate a crude SCP. This SCP is dried to generate a crude SCP product. This crude SCP is at least 55 wt % crude protein and less than 5 wt % ash. It also contains at least 0.2 wt % butyric acid.

Example 6: Production of Washed SCP from Wet-Mill Glucose Solution and at Least One Other Source The undried crude SCP from Example 5 is washed at least once with water to generate a washed SCP. This washed SCP is dried to generate a washed SCP product. This washed SCP is at least 55 wt % crude protein and less than 5 wt % ash. It also contains at least 0.2 wt % butyric acid.

Example 7: Production of SCP-Comprising Broth from Wet-Mill Glucose Solution Wet-mill processing creates a glucose solution from corn. Briefly, corn kernels are first steeped and then the germ, fiber, and protein fractions are removed, leaving a separated starch stream. This starch stream is then cooked and liquified and finally saccharified into a glucose solution. This glucose solution can be used as the primary carbon source in a fermentation to generate single cell protein (SCP).

For SCP production, the glucose solution is mixed with nutrients before fermentation. The nutrients can include, at a final concentration, $KH_2PO_4$ at 4.5 g/L, $MgSO_4 \cdot 7H_2O$ at 0.5 g/L, $FeSO_4 \cdot 7H_2O$ at 0.03 g/L, trace elements at 20 mL/L and vitamins at 20 mL/L. The trace elements solution is 2 g/L nitrilotriacetic acid, 1 g/L $MnSO_4 \cdot H_2O$, 0.8 g/L $Fe(SO_4)_2(NH_4)_2 \cdot 6H_2O$, 0.2 g/L $CoCl_2 \cdot 6H_2O$, 0.2 mg/L $ZnSO_4 \cdot 6H_2O$, 0.02 g/L $CuCl_2 \cdot 2H_2O$, 0.02 g/L $NiCl_2 \cdot 6H_2O$, 0.02 g/L $Na_2MoO_4 \cdot 2H_2O$, 0.02 g/L $Na_2SeO_4$, and 0.02 g/L $Na_2WO_4$. The vitamin solution is 2 mg/L biotin, 2 mg/L folic acid, 10 mg/L pyridoxine-HCl, 5 mg/L thiamine-HCl, 5 mg/L riboflavin, 5 mg/L nicotinic acid, 5 mg/L calcium D-(+)-pantothenate, 0.1 mg/L vitamin b12, 5 mg/L p-aminobenzoic acid, and 5 mg/L thioctic acid. Additionally, antifoam is added at 0.1 mL/L. The fermenter is inoculated with a culture of equal parts *Clostridium tryobutyricum* and *Butyribacterium methylotrophicum*, an acetogenic bacterium. The fermenter is sparged with $CO_2$ at <25 mL/min, controlled at 35-37° C., and pH bottom controlled at 6.5 with 8M NaOH. The fermentation is run to generate an SCP-comprising broth. The productivity of SCP production is at least 0.5 g/L/hr and the final yield is at least 15 wt % (g SCP/g glucose). The whole SCP-comprising broth is dried to generate a protein-rich product.

Example 8: Production of Crude SCP from Wet-Mill Glucose Solution

The SCP from the SCP-comprising broth in Example 7 is separated from the broth by centrifugation or other liquid/solid separation method to generate a crude SCP. This SCP is dried to generate a crude SCP product. This crude SCP is at least 55 wt % crude protein and less than 5 wt % ash. It also contains at least 0.2 wt % butyric acid.

Example 9: Production of Washed SCP from Wet-Mill Glucose Solution

The undried crude SCP from Example 8 is washed at least once with water to generate a washed SCP. This washed SCP is dried to generate a washed SCP product. This washed SCP is at least 55 wt % crude protein and less than 5 wt % ash. It also contains at least 0.2 wt % butyric acid.

Example 10: Production of SCP-Comprising Broth from Wet-Mill Glucose Solution and at Least One Other Source To the SCP fermentation in Example 7, at least one additional carbon source is added. These sources include: corn steep liquor, corn fiber, a blend of corn steep liquor and corn fiber, corn protein, corn starch, or liquified corn starch. The same nutrients and micronutrients can be added to the fermentation. The fermenter is inoculated and run as stated in Example 1, and an SCP-comprising broth is generated. SCP production is at least 0.5 g/L/hr and the yield is at least 15 wt %. The SCP-comprising broth is dried to generate a protein-rich product.

Example 11: Production of Crude SCP from Wet-Mill Glucose Solution and at Least One Other Source The SCP from the SCP-comprising broth in Example 10 is separated from the broth by centrifugation or other liquid/solid separation method to generate a crude SCP. This SCP is dried to generate a crude SCP product. This crude SCP is at least 55 wt % crude protein and less than 5 wt % ash. It also contains at least 0.2 wt % butyric acid.

Example 12: Production of Washed SCP from Wet-Mill Glucose Solution and at Least One Other Source The undried crude SCP from Example 11 is washed at least once with water to generate a washed SCP. This washed SCP is dried to generate a washed SCP product. This washed SCP is at least 55 wt % crude protein and less than 5 wt % ash. It also contains at least 0.2 wt % butyric acid.

Example 13: Production of Ethanol and a Protein Product from Wet-Mill Glucose Solution Wet-mill processing creates a glucose solution from corn. Briefly, corn kernels are first steeped and then the germ, fiber, and protein fractions are removed, leaving a separated starch stream. This starch stream is then cooked and liquified and finally saccharified into a glucose solution. This glucose solution is used as the primary carbon source in a fermentation to generate ethanol and single cell protein (SCP) simultaneously.

The glucose solution can be mixed with nutrients, micronutrients, and vitamins before fermentation. The fermenter is inoculated with a yeast strain to generate ethanol and equal parts *Clostridium tryobutyricum* and *Butyribacterium methylotrophicum*, an acetogenic bacterium. The fermenter is operated with an optional $CO_2$ sparge or pH control. The generated fermentation liquor contains both ethanol and SCP. The ethanol is separated from the liquor by distillation, and the solids are removed and dried to generate a protein product.

Example 14: Production of Ethanol and a Protein Product from Wet-Mill Glucose Solution and at Least One Other Source To the fermentation in Example 13, at least one additional carbon source is added. These sources include: corn steep liquor, corn fiber, a blend of corn steep liquor and corn fiber, corn protein, corn starch, or liquified corn starch. The same nutrients, micronutrients, or vitamins can be added to the fermentation. The fermenter is inoculated and run as stated in Example 10, and a fermentation liquor is generated comprising ethanol and SCP. The ethanol is separated from the liquor by distillation, and the solids are removed and dried to generate a protein product.

Example 15: Production of SCP-Comprising Broth from Wet-Mill Glucose Solution

Wet-mill processing creates a glucose solution from corn. Briefly, corn kernels are first steeped and then the germ, fiber, and protein fractions are removed, leaving a separated starch stream. This starch stream is then cooked and liquified and finally saccharified into a glucose solution. This glucose solution can be used as the primary carbon source for the production of a bioproduct, like lysine, or in a fermentation to generate single cell protein (SCP).

For SCP production, the glucose solution is mixed with nutrients before fermentation. The nutrients can include, at a final concentration, $KH_2PO_4$ at 4.5 g/L, $MgSO_4.7H_2O$ at 0.5 g/L, $FeSO_4.7H_2O$ at 0.03 g/L, trace elements at 20 mL/L and vitamins at 20 mL/L. The trace elements solution is 2 g/L nitrilotriacetic acid, 1 g/L $MnSO_4.H_2O$, 0.8 g/L Fe $(SO_4)_2(NH_4)_2.6H_2O$, 0.2 g/L $CoCl_2.6H_2O$, 0.2 mg/L $ZnSO_4.6H_2O$, 0.02 g/L $CuCl_2.2H_2O$, 0.02 g/L $NiCl_2.6H_2O$, 0.02 g/L $Na_2MoO_4.2H_2O$, 0.02 g/L $Na_2SeO_4$, and 0.02 g/L $Na_2WO_4$. The vitamin solution is 2 mg/L biotin, 2 mg/L folic acid, 10 mg/L pyridoxine-HCl, 5 mg/L thiamine-HCl, 5 mg/L riboflavin, 5 mg/L nicotinic acid, 5 mg/L calcium D-(+)-pantothenate, 0.1 mg/L vitamin b12, 5 mg/L. The fermenter is inoculated with a culture of equal parts *Clostridium tryobutyricum* and *Butyribacterium methylotrophicum*, an acetogenic bacterium. The fermenter is sparged with $CO_2$ at <25 mL/min, controlled at 35-37° C., and pH bottom controlled at 6.5 with 8M NaOH. The fermentation is run to generate an SCP-comprising broth. The productivity of SCP production is at least 0.5 g/L/hr and the final yield is at least 15 wt % (g SCP/g glucose). The whole SCP-comprising broth is dried to generate a protein-rich product.

Example 16: Production of Crude SCP from Wet-Mill Glucose Solution

The SCP from the SCP-comprising broth in Example 15 is separated from the broth by centrifugation or other liquid/solid separation method to generate a crude SCP. This SCP is dried to generate a crude SCP product. This crude SCP is at least 55 wt % crude protein and less than 5 wt % ash. It also contains at least 0.2 wt % butyric acid.

Example 17: Production of Washed SCP from Wet-Mill Glucose Solution

The undried crude SCP from Example 16 is washed at least once with water to generate a washed SCP. This washed SCP is dried to generate a washed SCP product. This washed SCP is at least 55 wt % crude protein and less than 5 wt % ash. It also contains at least 0.2 wt % butyric acid.

Example 18: Production of SCP-Comprising Broth from a Residual Fermentation Broth The glucose solution from Example 15 is first used to generate lysine, for example from the fermentation of *Corynebacterium glutamicum*. Lysine is separated from the fermentation broth to produce a liquid residue composed of residual carbohydrate, byproducts of the *Corynebacterium glutamicum* fermentation, and other fermentation solids. This liquid residue is then inoculated with equal parts *Clostridium tryobutyricum* and *Butyribacterium methylotrophicum*, an acetogenic bacterium. The fermenter is sparged with $CO_2$ at <25 mL/min, controlled at 35-37° C., and pH bottom controlled at 6.5 with 8M NaOH. The fermentation is run to generate an SCP-comprising broth. The productivity of SCP production is at least 0.5 g/L/hr and the final yield is at least 15 wt % (g SCP/g glucose). The whole SCP-comprising broth is dried to generate a protein-rich product.

Example 19: Production of Crude SCP from a Residual Fermentation Broth

The SCP from the SCP-comprising broth in Example 18 is separated from the broth by centrifugation or other liquid/solid separation method to generate a crude SCP. This SCP is dried to generate a crude SCP product. This crude SCP is at least 55 wt % crude protein and less than 5 wt % ash. It also contains at least 0.2 wt % butyric acid.

Example 20: Production of Washed SCP from a Residual Fermentation Broth

The undried crude SCP from Example 19 is washed at least once with water to generate a washed SCP. This washed SCP is dried to generate a washed SCP product. This washed SCP is at least 55 wt % crude protein and less than 5 wt % ash. It also contains at least 0.2 wt % butyric acid.

Example 21: Production of SCP-Comprising Broth from Wet-Mill Glucose Solution and at Least One Other Source To the SCP fermentation in Example 15, at least one additional carbon source is added. These sources include: corn steep liquor, corn fiber, a blend of corn steep liquor and corn fiber, corn protein, corn starch, liquid residue from the first bioproduct fermentation (for example lysine production), a blend of corn steep liquor and liquid residue, a blend of corn fiber, corn steep liquor and liquid residue, or liquified corn starch. The same nutrients and micronutrients can be added to the fermentation. The fermenter is inoculated and run as stated in Example 15, and an SCP-comprising broth is generated. SCP production is at least 0.5 g/L/hr and the yield is at least 15 wt %. The SCP-comprising broth is dried to generate a protein-rich product.

Example 22: Production of Crude SCP from Wet-Mill Glucose Solution and at Least One Other Source The SCP from the SCP-comprising broth in Example 21 is separated from the broth by centrifugation or other liquid/solid separation method to generate a crude SCP. This SCP is dried to generate a crude SCP product. This crude SCP is at least 55 wt % crude protein and less than 5 wt % ash. It also contains at least 0.2 wt % butyric acid.

Example 23: Production of Washed SCP from Wet-Mill Glucose Solution and at Least One Other Source The undried crude SCP from Example 22 is washed at least once with water to generate a washed SCP. This washed SCP is dried to generate a washed SCP product. This washed SCP is at least 55 wt % crude protein and less than 5 wt % ash. It also contains at least 0.2 wt % butyric acid.

The invention claimed is:

1. An integrated method for the production of ethanol and a single cell protein product, comprising:
   (i) providing corn kernels, which kernels comprise germ, fiber, protein and starch;
   (ii) steeping said corn kernels, whereby steeped corn kernels and steep liquor are formed;
   (iii) separating said steeped kernels from said steep liquor, whereby separated steeped kernels and separated steep liquor are formed, which separated steep liquor comprises a first carbon source;
   (iv) optionally, concentrating said separated steep liquor by water removal therefrom, whereby concentrated steep liquor is formed;
   (v) mechanically separating germ from said separated steeped kernel, whereby separated germ is formed;
   (vi) mechanically separating fiber from said separated steeped kernel, whereby separated fiber is formed, which separated fiber comprises a second carbon source;
   (vii) optionally, blending separated fiber with separated steep liquor and/or with concentrated steep liquor, whereby a first blend is formed;
   (viii) separating starch from protein in said steeped kernel, whereby separated starch and a separated protein composition are formed, which separated protein composition comprises a third carbon source and which separated starch comprises a fourth carbon source;
   (ix) cooking and liquefying said separated starch, whereby liquefied starch is formed;
   (x) saccharifying said liquefied starch, whereby a glucose solution is formed;
   (xi) culturing yeast in said glucose solution for a specific duration, whereby $CO_2$ and an ethanol comprising fermentation liquor are formed;
   (xii) distilling ethanol from said fermentation liquor, whereby separated ethanol and stillage are formed, which stillage comprises a fifth carbon source, which fifth carbon source comprises residual carbohydrate and optionally byproduct glycerol;
   (xiii) optionally, blending separated fiber with separated steep liquor and/or with concentrated steep liquor and with said stillage, whereby a second blend is formed;
   (xiv) providing a fermentation medium comprising said fifth carbon source; and $CO_2$;
   (xv) culturing a selected organism in said fermentation medium, whereby said carbon source is metabolized and an SCP-comprising broth is formed, at a given yield and given productivity of biomass production;
   (xvi) optionally, separating SCP from said SCP-comprising broth, whereby crude SCP and a residue is formed;
   (xvii) optionally washing said crude SCP, whereby washed SCP is formed; and (xviii) drying said SCP-comprising broth, said crude SCP or said washed SCP;
   wherein
   the combined carbon content of said residual carbohydrate and said byproduct glycerol in said fermentation liquor is at least 3% of that in the carbohydrate of said glucose solution; and
   said selected organism comprises an acetogenic organism selected from the group consisting of *Butyribacterium methylotrophicum, Blautia product, Clostridium drakei, Clostridium magnum, Clostridium scatologenes, Clostridium ljungdahlii, Clostridium autoethanogenum, Clostridium aceticum, Clostridium ragsdalei, Clostridium carboxidivorans, Eubacterium aggregans, Eubacterium limosum, Acetobacterium woodii, Oxobacter pfennigii, Treponema azotonutricium, Sporosoma ovata, Sporosoma termitida,* and *Terriporobacter glycolicus.*

2. The method of claim 1, wherein said culturing yeast specific duration is selected so that less than 95% by weight of the carbohydrates in said glucose solution is metabolized.

3. The method of claim 1, wherein said selected organism further comprises an organism capable of metabolizing glycerol, oligosaccharides or a combination thereof.

4. The method of claim 1, wherein said culturing selected organism is anaerobic.

5. The method of claim 1, further comprises adding an exogenous carbon source to said fermentation medium, wherein said exogenous carbon source is metabolized in said culturing selected organism.

6. The method of claim 1, wherein SCP generation productivity is at least 0.5 g/L/hr.

7. The method of claim 1, wherein crude protein content of said crude SCP or said washed SCP on dry basis is at least 55% by weight.

8. The method of claim 1, wherein said crude SCP or said washed SCP comprises at least 0.2% by weight butyric acid on dry basis.

9. An integrated method for the production of water-soluble bioproduct and a single cell protein product, comprising:
   (i) providing corn kernels, which kernels comprise germ, fiber, protein and starch;
   (ii) steeping said corn kernels, whereby steeped corn kernels and steep liquor are formed;
   (iii) separating said steeped kernels from said steep liquor, whereby separated steeped kernels and separated steep liquor are formed, which separated steep liquor comprises a first carbon source;
   (iv) optionally, concentrating said separated steep liquor by water removal therefrom, whereby concentrated steep liquor is formed;

(v) mechanically separating germ from said separated steeped kernel, whereby separated germ is formed;

(vi) mechanically separating fiber from said separated steeped kernel, whereby separated fiber is formed, which separated fiber comprises a second carbon source;

(vii) optionally, blending separated fiber with separated steep liquor and/or with concentrated steep liquor, whereby a first blend is formed;

(viii) separating starch from protein in said steeped kernel, whereby separated starch and a separated protein composition are formed, which separated protein composition comprises a third carbon source and which separated starch comprises a fourth carbon source;

(ix) cooking and liquefying said separated starch, whereby liquefied starch is formed;

(x) saccharifying said liquefied starch, whereby a glucose solution is formed;

(xi) culturing a first organism in said glucose solution for a specific duration, whereby a fermentation liquor is formed, which fermentation liquor comprises a water soluble bioproduct;

(xii) separating bioproduct from said fermentation liquor, whereby separated bioproduct and a liquid residue are formed, which residue comprises a fifth carbon source, and which fifth carbon source comprises residual carbohydrate and optionally byproduct glycerol;

(xiii) optionally, blending separated fiber with separated steep liquor and/or with concentrated steep liquor and with said residue, whereby a second blend is formed;

(xiv) providing a fermentation medium comprising said fifth carbon source and CO2;

(xv) culturing a selected second organism in said fermentation medium, whereby said carbon source is metabolized and an SCP-comprising broth is formed, at a given yield and given productivity of biomass production;

(xvi) optionally, separating SCP from said SCP-comprising broth, whereby crude SCP and a residue is formed;

(xvii) optionally washing said crude SCP, whereby washed SCP is formed; and (xviii) drying said SCP-comprising broth, said crude SCP or said washed SCP; wherein the combined carbon content of said residual carbohydrate and said byproduct glycerol in said fermentation liquor is at least 3% of that in the carbohydrate of said glucose solution; and said selected second organism comprises an acetogenic organism selected from the group consisting of *Butyribacterium methylotrophicum, Blautia product, Clostridium drakei, Clostridium magnum, Clostridium scatologenes, Clostridium ljungdahlii, Clostridium autoethanogenum, Clostridium aceticum, Clostridium ragsdalei, Clostridium carboxidivorans, Eubacterium aggregans, Eubacterium limosum, Acetobacterium woodii, Oxobacter pfennigii, Treponema azotonutricium, Sporosoma ovata, Sporosoma termitida,* and *Terriporobacter glycolicus.*

10. The method of claim 9, wherein said fermentation liquor comprises at least 10% by weight bioproduct.

11. The method of claim 9, wherein said selected second organism further comprises an organism capable of metabolizing glycerol, oligosaccharides or a combination thereof.

12. The method of claim 9, further comprises adding an exogenous carbon source to said fermentation medium, wherein said exogenous carbon source is metabolized in said culturing selected organism.

13. The method of claim 9, wherein crude protein content of said crude SCP or said washed SCP on dry basis is at least 55% by weight.

14. The method of claim 9, wherein said crude SCP or said washed SCP comprises at least 0.2% by weight butyric acid on dry basis.

15. The method of claim 9, wherein said bioproduct is lysine.

16. The method of claim 9, wherein said bioproduct is lactic acid.

* * * * *